(12) United States Patent
Howard et al.

(10) Patent No.: US 11,020,586 B2
(45) Date of Patent: *Jun. 1, 2021

(54) DISTALLY CURVED ELECTRICAL STIMULATION LEAD AND METHODS OF MAKING AND USING

(71) Applicant: Boston Scientific Neuromodulation Corporation, Valencia, CA (US)

(72) Inventors: Joshua Dale Howard, Sacramento, CA (US); Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 523 days.

This patent is subject to a terminal disclaimer.

(21) Appl. No.: 15/889,930

(22) Filed: Feb. 6, 2018

(65) Prior Publication Data
US 2018/0154139 A1    Jun. 7, 2018

Related U.S. Application Data

(63) Continuation of application No. 13/900,889, filed on May 23, 2013, now Pat. No. 9,919,148.
(Continued)

(51) Int. Cl.
*A61N 1/05* (2006.01)
(52) U.S. Cl.
CPC .......... *A61N 1/0551* (2013.01); *A61N 1/0556* (2013.01); *A61N 1/0558* (2013.01)
(58) Field of Classification Search
CPC ... A61N 1/0551; A61N 1/0556; A61N 1/0558
See application file for complete search history.

(56) References Cited

U.S. PATENT DOCUMENTS

| 3,333,045 A | 7/1967 | Fisher et al. |
| 3,918,440 A | 11/1975 | Kraus |

(Continued)

FOREIGN PATENT DOCUMENTS

| AU | 2012201634 A1 | 4/2012 |
| WO | 2003020365 A1 | 3/2003 |

(Continued)

OTHER PUBLICATIONS

Official Communication for U.S. Appl. No. 13/900,889, dated Nov. 21, 2014.

(Continued)

*Primary Examiner* — Alyssa M Alter
(74) *Attorney, Agent, or Firm* — Branch Partners PLLC; Bruce E. Black

(57) ABSTRACT

An implantable electrical stimulation lead including a lead body having a distal end, a proximal end, and a longitudinal length, wherein the distal end of the lead body is formed into a hook or coil shape; a plurality of electrodes disposed along the hook or coil at the distal end of the lead body; a plurality of terminals disposed on the proximal end of the lead body; and a plurality of conductors, each conductor electrically coupling at least one of the electrodes to at least one of the terminals. The lead can be used to stimulate, for example, a dorsal root ganglion with the hook-shaped or coil-shaped distal end disposed around a portion of the dorsal root ganglion.

20 Claims, 9 Drawing Sheets

Related U.S. Application Data

(60) Provisional application No. 61/651,830, filed on May 25, 2012.

(56) References Cited

U.S. PATENT DOCUMENTS

| | | | |
|---|---|---|---|
| 5,143,090 A | 9/1992 | Dutcher et al. |
| 5,217,028 A | 6/1993 | Dutcher et al. |
| 5,330,477 A | 7/1994 | Cook |
| 5,738,521 A | 4/1998 | Dugot |
| 5,876,431 A | 3/1999 | Spehr et al. |
| 6,104,957 A | 8/2000 | Alo et al. |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,902,547 B2 | 6/2005 | Aves et al. |
| 7,244,150 B1 | 7/2007 | Brase et al. |
| 7,337,005 B2 | 2/2008 | Kim et al. |
| 7,337,006 B2 | 2/2008 | Kim et al. |
| 7,437,193 B2 | 10/2008 | Parramon et al. |
| 7,447,546 B2 | 11/2008 | Kim et al. |
| 7,450,993 B2 | 11/2008 | Kim et al. |
| 7,450,997 B1 | 11/2008 | Pianca et al. |
| 7,502,651 B2 | 3/2009 | Kim et al. |
| 7,580,753 B2 | 8/2009 | Kim et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 7,993,378 B2 | 8/2011 | Foley et al. |
| 8,082,039 B2 | 12/2011 | Kim et al. |
| 8,175,710 B2 | 5/2012 | He |
| 8,204,595 B2 | 6/2012 | Pianca et al. |
| 8,224,450 B2 | 7/2012 | Brase |
| 8,229,565 B2 | 7/2012 | Kim et al. |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmerman et al. |
| 8,647,346 B2 | 2/2014 | Bleich et al. |
| 8,688,235 B1 | 4/2014 | Pianca et al. |
| 8,712,546 B2 | 4/2014 | Kim et al. |
| 8,768,488 B2 | 7/2014 | Barker |
| 8,774,926 B2 | 7/2014 | Alataris et al. |
| 8,831,742 B2 | 9/2014 | Pianca et al. |
| 8,897,893 B2 | 11/2014 | Pianca |
| 8,983,624 B2 | 3/2015 | Imran |
| 9,089,694 B2 | 7/2015 | Pianca |
| 9,199,074 B2 | 12/2015 | Pianca |
| 9,205,259 B2 | 12/2015 | Kim et al. |
| 9,205,260 B2 | 12/2015 | Kim et al. |
| 9,259,569 B2 | 2/2016 | Brounstein et al. |
| 2005/0033374 A1 | 2/2005 | Gerber |
| 2005/0240238 A1 | 10/2005 | Mamo et al. |
| 2007/0150036 A1 | 6/2007 | Anderson |
| 2007/0239248 A1 | 10/2007 | Hastings et al. |
| 2007/0265682 A1 | 11/2007 | Wiegnann et al. |
| 2008/0071320 A1 | 3/2008 | Brase |
| 2008/0140152 A1 | 6/2008 | Imran et al. |
| 2008/0140153 A1 | 6/2008 | Burdulis |
| 2008/0140169 A1 | 6/2008 | Imran |
| 2008/0262588 A1 | 10/2008 | Zarembo et al. |
| 2009/0187222 A1 | 7/2009 | Barker |
| 2009/0204193 A1 | 8/2009 | Kokones et al. |
| 2009/0276021 A1 | 11/2009 | Meadows et al. |
| 2009/0276025 A1 | 11/2009 | Burnes et al. |
| 2010/0076535 A1 | 3/2010 | Pianca et al. |
| 2010/0137938 A1 | 6/2010 | Kishawi et al. |
| 2010/0179562 A1 | 7/2010 | Linker et al. |
| 2010/0241179 A1 | 9/2010 | Gielen et al. |
| 2010/0249875 A1* | 9/2010 | Kishawi ............ A61N 1/36157 607/46 |
| 2010/0268298 A1 | 10/2010 | Moffitt et al. |
| 2010/0274336 A1 | 10/2010 | Nguyen-Stella et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0213445 A1 | 9/2011 | Blischak |
| 2011/0238129 A1 | 9/2011 | Moffitt et al. |
| 2011/0276056 A1 | 11/2011 | Grigsby et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0101326 A1 | 4/2012 | Simon et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |
| 2013/0325091 A1 | 12/2013 | Pianca et al. |
| 2014/0018885 A1 | 1/2014 | Pianca |
| 2014/0039587 A1 | 2/2014 | Romero |
| 2014/0257240 A1 | 9/2014 | Burdulis |
| 2014/0276925 A1 | 9/2014 | Alves et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0099936 A1 | 4/2015 | Burdulis et al. |
| 2015/0151113 A1 | 6/2015 | Govea et al. |

FOREIGN PATENT DOCUMENTS

| | | |
|---|---|---|
| WO | 2003084398 A1 | 10/2003 |
| WO | 2005120203 A2 | 12/2005 |
| WO | 2006029257 A2 | 3/2006 |
| WO | 2007041604 A2 | 4/2007 |
| WO | 2010083308 A1 | 7/2010 |

OTHER PUBLICATIONS

Official Communication for U.S. Appl. No. 13/900,889, dated Apr. 28, 2015.

Official Communication for U.S. Appl. No. 13/900,889, dated Sep. 24, 2015.

* cited by examiner

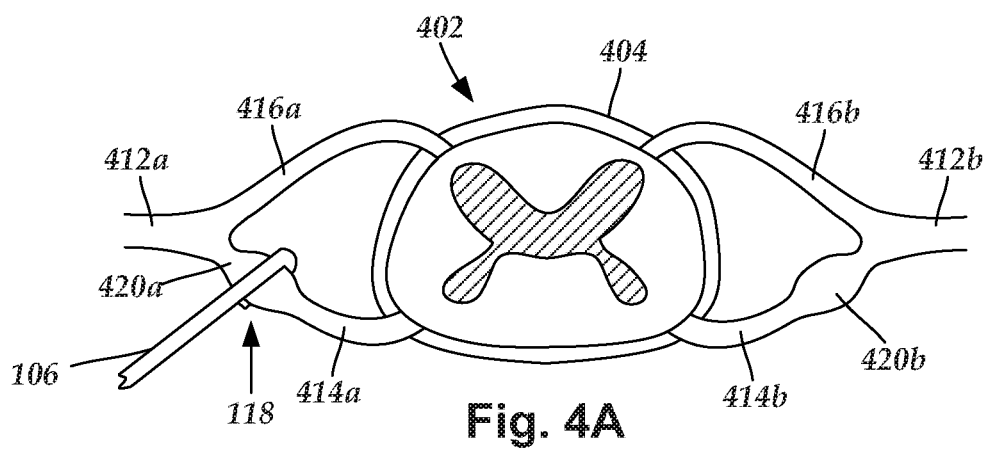
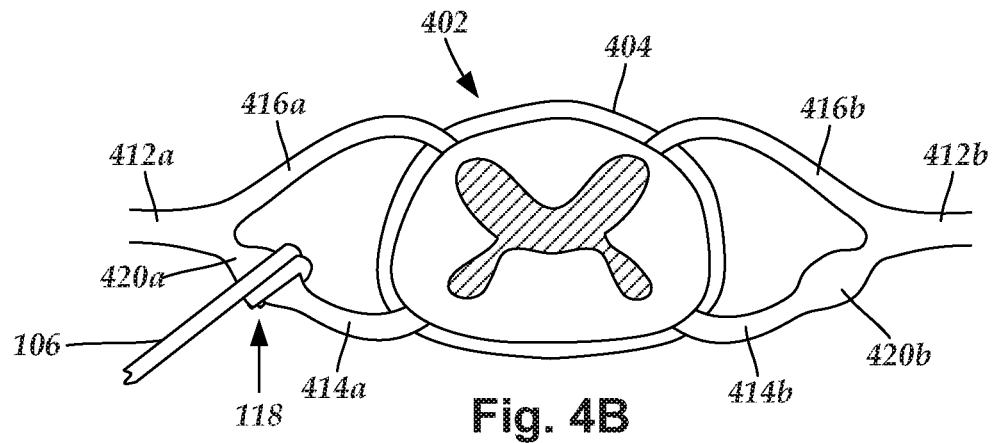

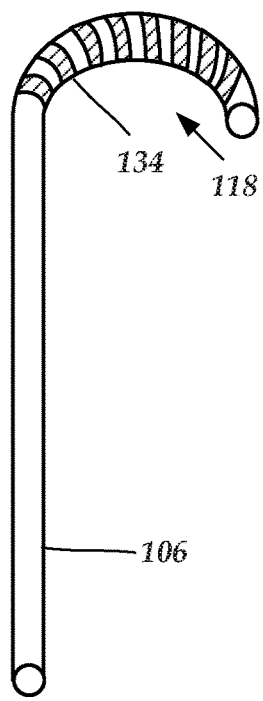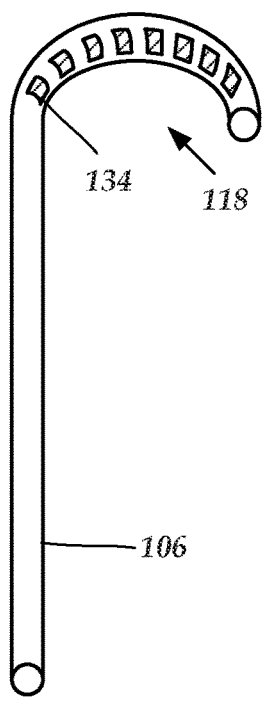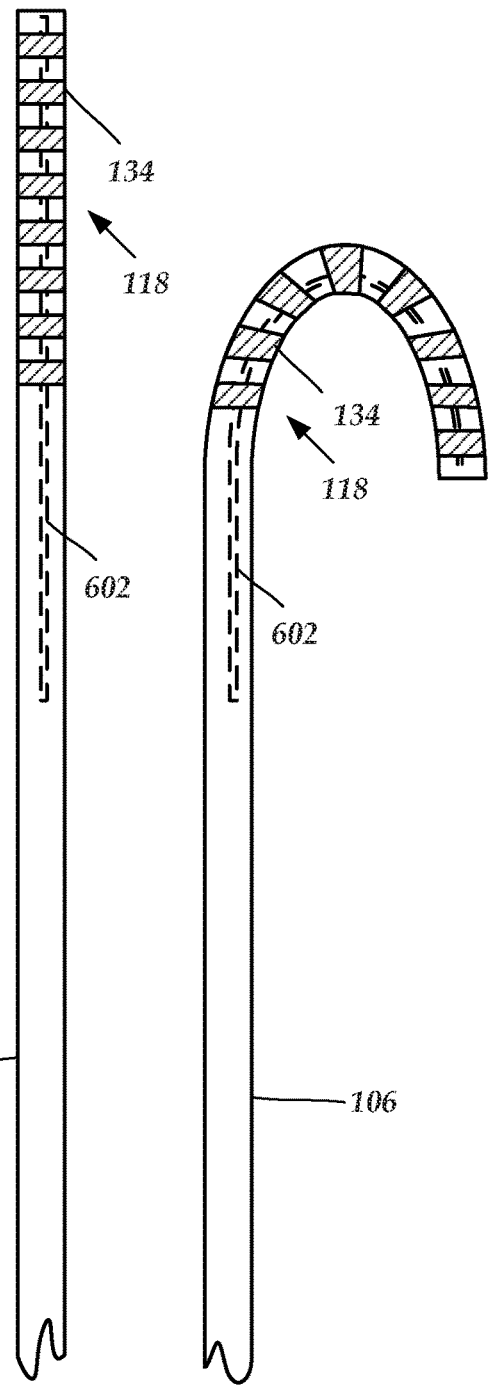
Fig. 5A  Fig. 5B  Fig. 6A  Fig. 6B

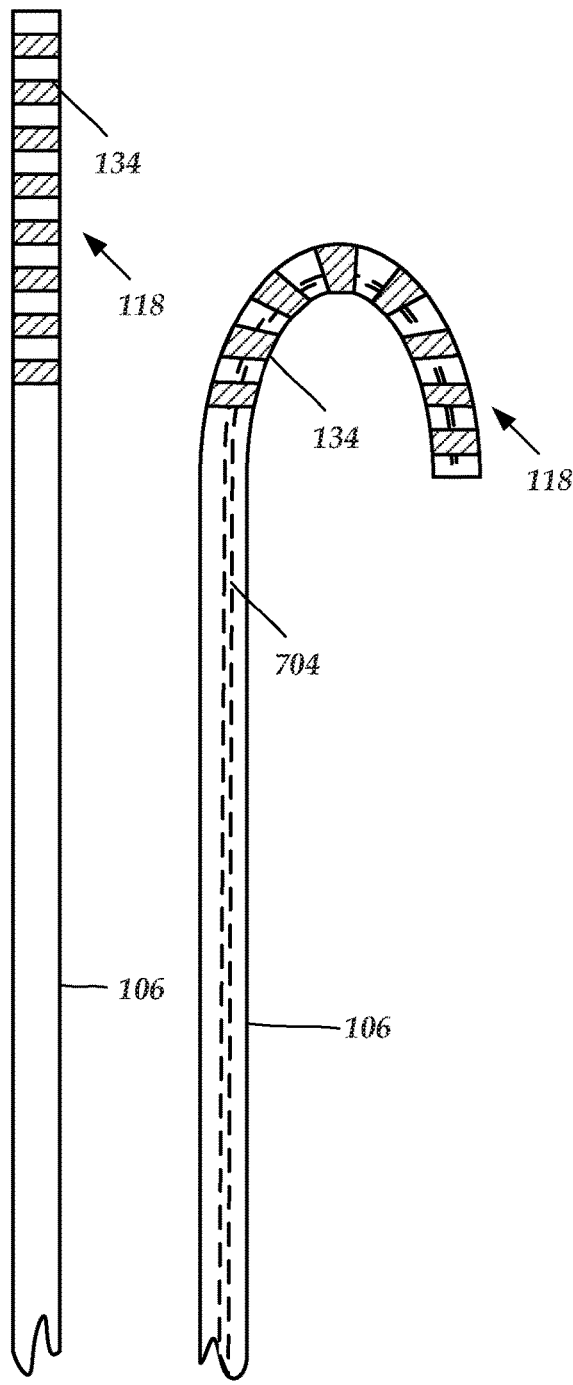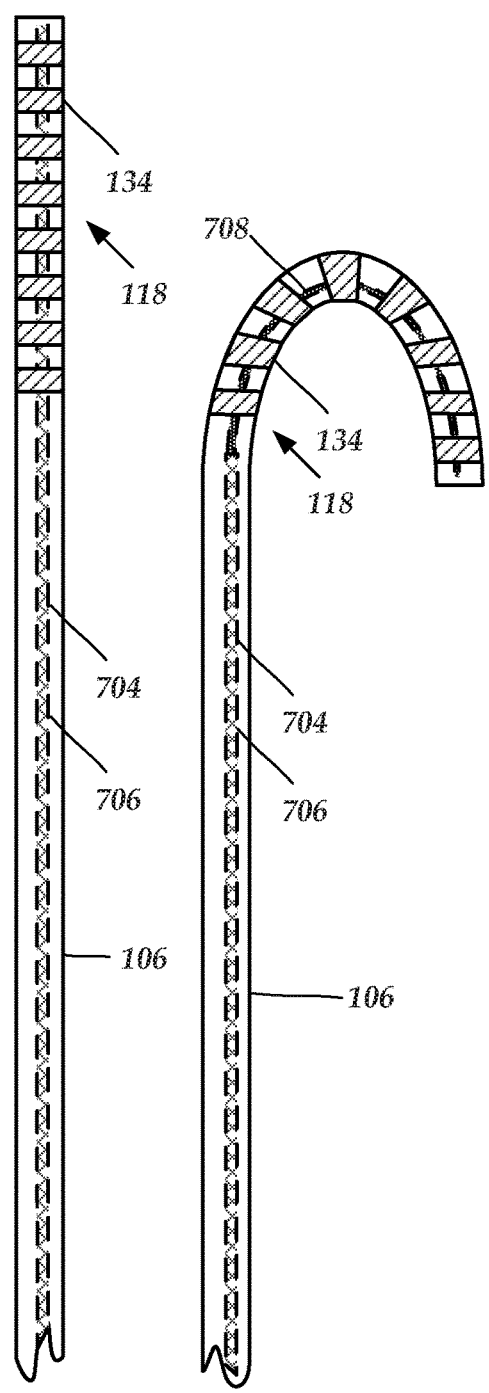
Fig. 7A  Fig. 7B          Fig. 8A  Fig. 8B

DISTALLY CURVED ELECTRICAL STIMULATION LEAD AND METHODS OF MAKING AND USING

CROSS-REFERENCE TO RELATED APPLICATIONS

This application is a continuation of U.S. patent application Ser. No. 13/900,889 filed on May 23, 2013, which claims the benefit under 35 U.S.C. § 119(e) of U.S. Provisional Patent Application Ser. No. 61/651,830 filed on May 25, 2012, both of which are incorporated herein by reference.

FIELD

The present invention is directed to the area of implantable electrical stimulation systems and methods of making and using the systems. The present invention is also directed to implantable electrical stimulation leads having a distal end formed in a hook or coil shape to fit around tissue to be stimulated, as well as methods of making and using the leads and electrical stimulation systems containing the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an implantable electrical stimulation lead including a lead body having a distal end, a proximal end, and a longitudinal length, wherein the distal end of the lead body is formed into a curved hook; a plurality of electrodes disposed along the curved hook at the distal end of the lead body; a plurality of terminals disposed on the proximal end of the lead body; and a plurality of conductors, each conductor electrically coupling at least one of the electrodes to at least one of the terminals.

Another embodiment is a method of implanting an electrical stimulation lead including providing the electrical stimulation lead described above and implanting the electrical stimulation lead with the curved hook disposed around a dorsal root ganglion of a patient. A portion of the lead adjacent to the distal end extends at an angle of at least 45° with respect to a dorsal root extending from the dorsal root ganglion.

A further embodiment is an implantable electrical stimulation lead including a lead body having a distal end, a proximal end, and a longitudinal length; a plurality of electrodes disposed along the distal end of the lead body; a plurality of terminals disposed on the proximal end of the lead body; a plurality of conductors, each conductor electrically coupling at least one of the electrodes to at least one of the terminals; and a bendable shaping member disposed within at least the distal end of the lead body. The bendable shaping member is reversibly bendable and permits formation of a hook or coil shape in the distal end of the lead body by bending of the distal end of the lead body into the hook or coil shape. The bendable shaping member is configured and arranged to retain the distal end of the lead body in the hook or coil shape without external force being applied.

Yet another embodiment is a method of implanting an electrical stimulation lead including providing the electrical stimulation lead of preceding paragraph; shaping the distal end of the electrical stimulation lead into a hook or coil shape by bending the bendable shaping member; and implanting the electrical stimulation lead with the distal end in the hook or coil shape disposed around a dorsal root ganglion of a patient.

Another embodiment is a method of implanting a lead including providing a lead comprising a lead body having a distal end, a proximal end, and a longitudinal length, a plurality of electrodes disposed along the distal end of the lead body, a plurality of terminals disposed on the proximal end of the lead body, and a plurality of conductors, each conductor electrically coupling at least one of the electrodes to at least one of the terminals. The method also includes inserting a guidewire or stylet into the lead; and implanting the lead into the patient and around at least a portion of dorsal root ganglion of the patient using the guidewire or stylet to shape the distal end of the lead body into a hook or coil situated around the portion of the dorsal root ganglion.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of a portion of the spinal cord of FIG. 3A disposed in a portion of a vertebral column with the dorsal root ganglia of FIG. 3A extending outward from the vertebral column and one embodiment of a lead having distal end with a hook shape disposed around a dorsal root ganglion, according to the invention;

FIG. 4B is a schematic perspective view of a portion of the spinal cord of FIG. 3A disposed in a portion of a vertebral column with the dorsal root ganglia of FIG. 3A extending outward from the vertebral column and another embodiment of a lead having distal end with a coil shape disposed around a dorsal root ganglion, according to the invention;

FIG. 5A is a schematic perspective view of one embodiment of a distal end of an electrical stimulation lead formed in a hook shape, according to the invention;

FIG. 5B is a schematic perspective view of another embodiment of a distal end of an electrical stimulation lead formed in a hook shape, according to the invention;

FIG. 6A is a schematic side view of one embodiment of a distal portion of an electrical stimulation lead with a bendable shaping member disposed therein, according to the invention;

FIG. 6B is a schematic side view of the electrical stimulation lead of FIG. 6A with the distal end of the lead bent into a hook shape using the bendable shaping member, according to the invention;

FIG. 7A is a schematic side view of one embodiment of a distal portion of an electrical stimulation lead, according to the invention;

FIG. 7B is a schematic side view of the electrical stimulation lead of FIG. 7A with the distal end of the lead bent into a hook shape using a guidewire or stylet inserted into the lead, according to the invention;

FIG. 8A is a schematic side view of one embodiment of a distal portion of an electrical stimulation lead with guidewire or stylet inserted therein, according to the invention;

FIG. 8B is a schematic side view of the electrical stimulation lead of FIG. 8A with the distal end of the lead bent into a hook shape using a curved inner member of the guidewire or stylet, according to the invention;

DETAILED DESCRIPTION

The present invention is directed to the area of implantable electrical stimulation systems and methods of making and using the systems. The present invention is also directed to implantable electrical stimulation leads having a distal end formed in a hook or coil shape to fit around tissue to be stimulated, as well as methods of making and using the leads and electrical stimulation systems containing the leads.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; and 2012/0316615; and U.S. patent application Ser. Nos. 12/177,823; 13/667,953; and 13/750,725, all of which are incorporated by reference.

Figure 1:
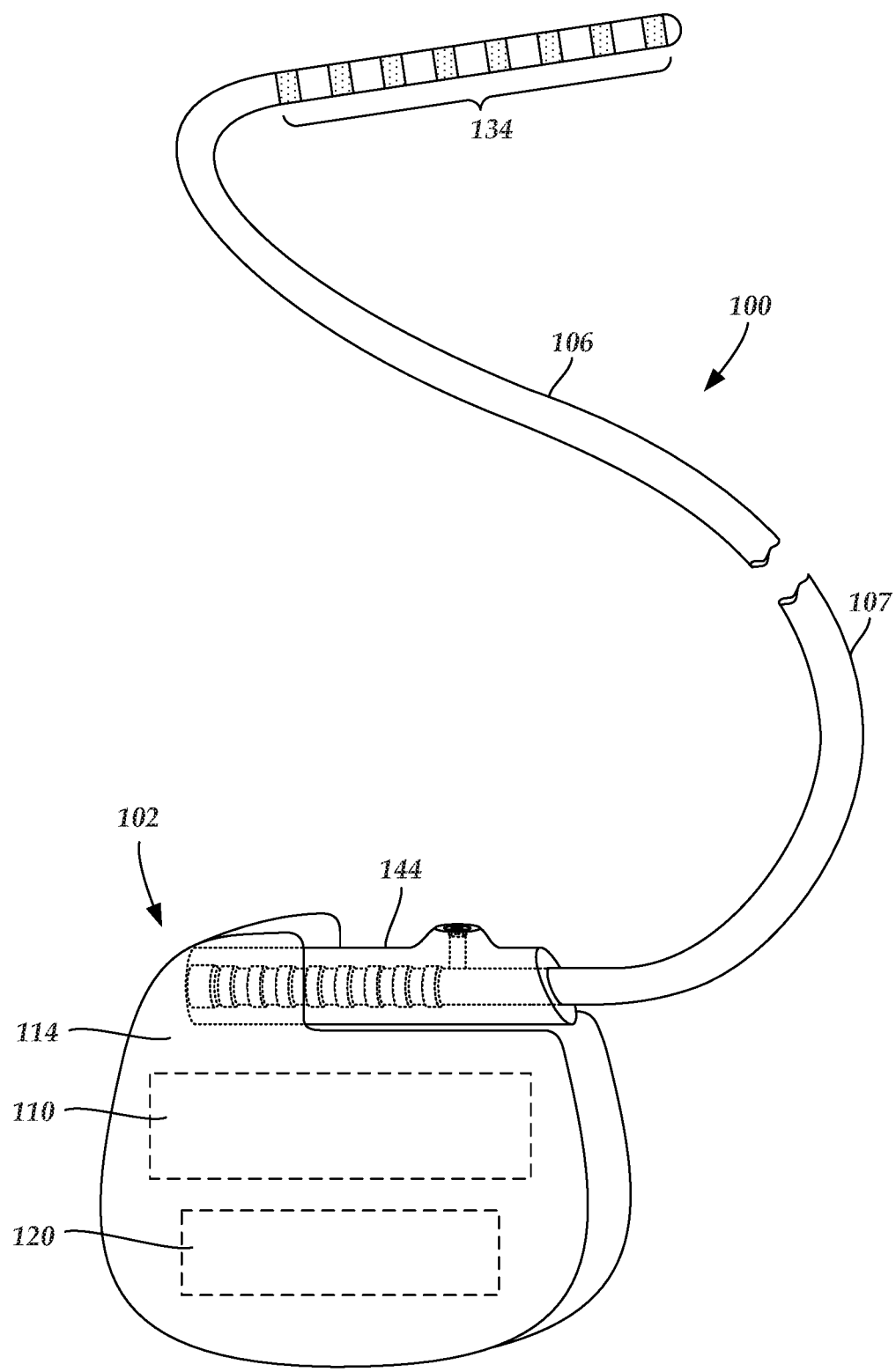
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead 106 coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106 and forms a lead body 107.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134.

The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet wire to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
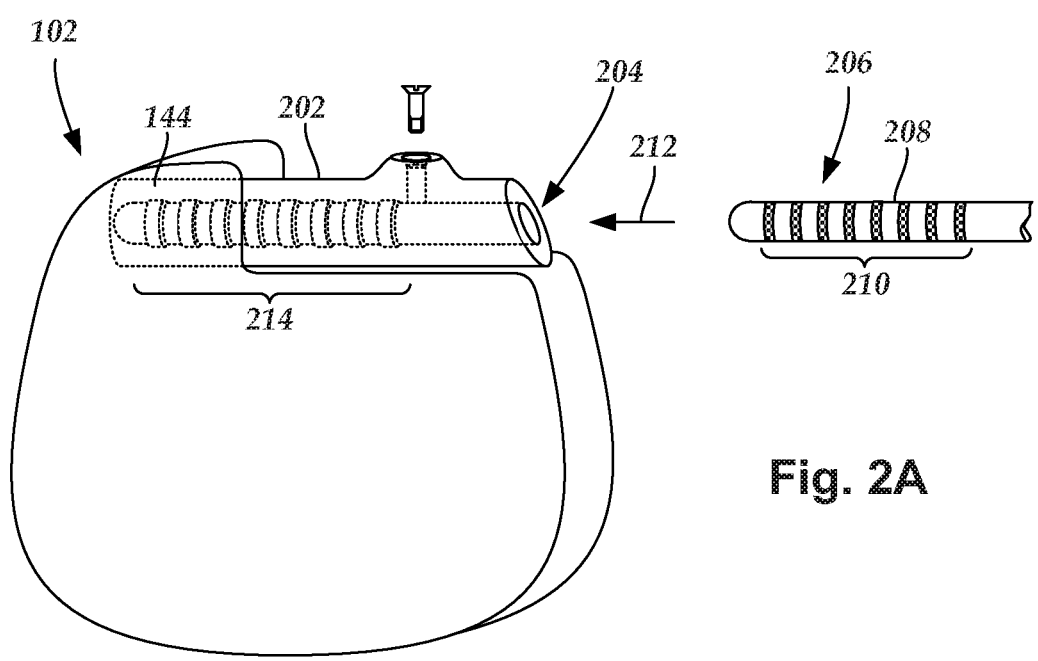
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat. Nos. 7,244,150 and 8,224,450, which are incorporated by reference.

Figure 2B:
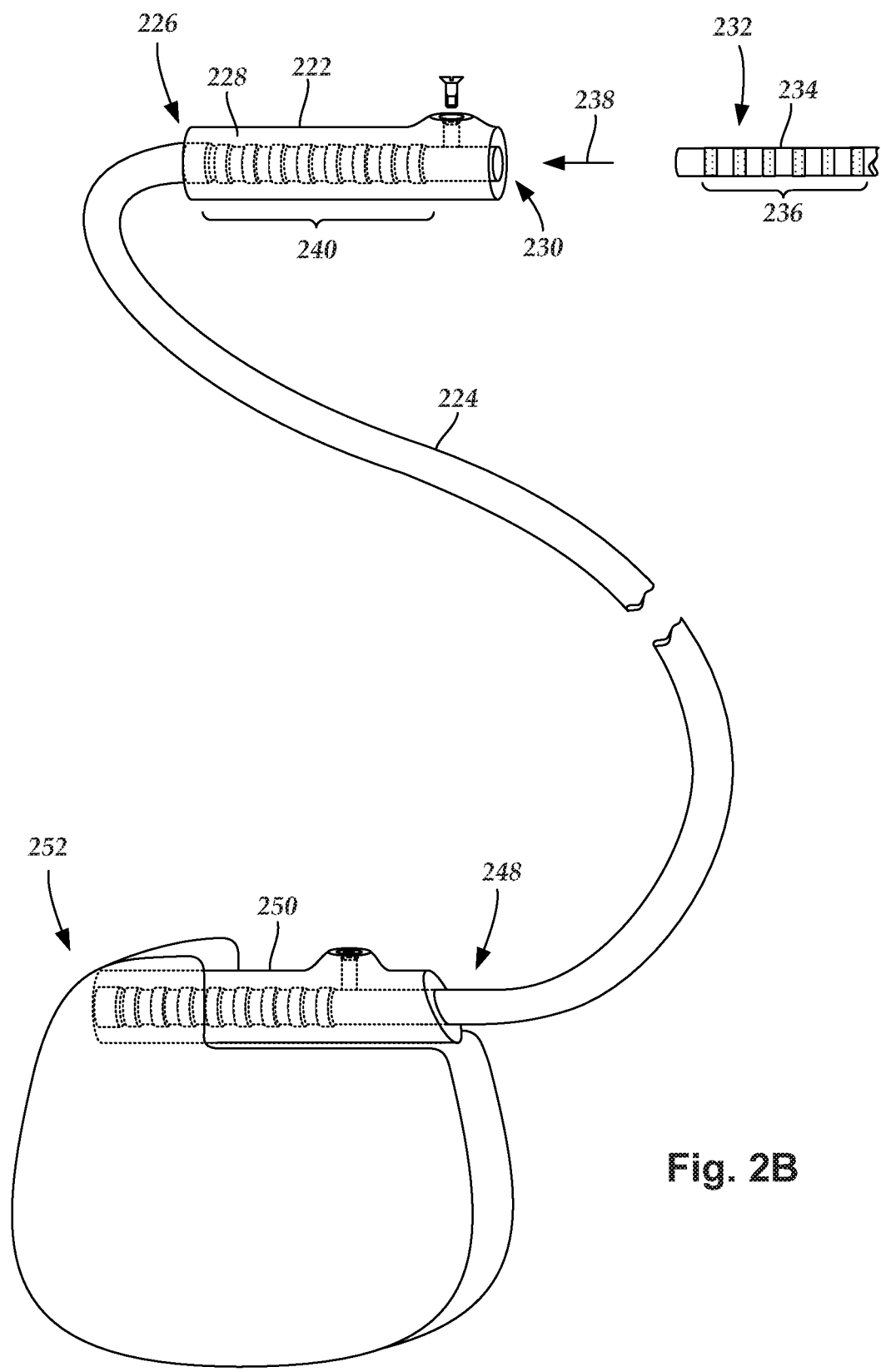
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Figure 3A:
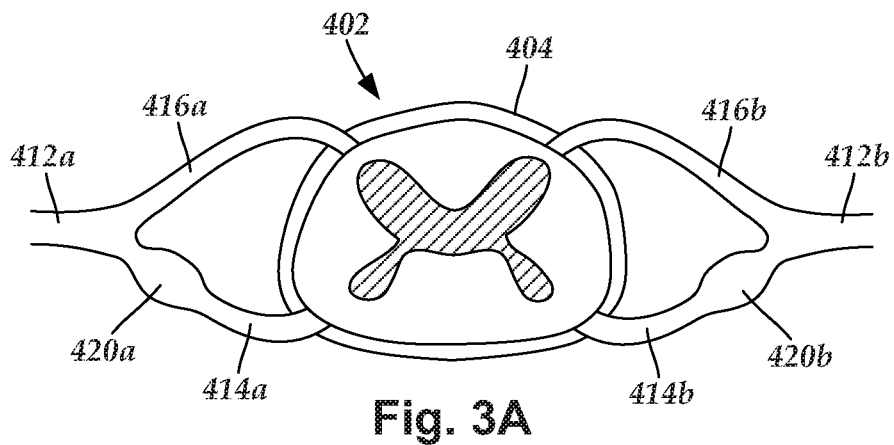
FIG. 3A is a schematic transverse cross-sectional view of spinal nerves extending from a spinal cord, the spinal nerves including dorsal root ganglia.

Turning to FIG. 3A, one potential target stimulation location is the dorsal root ganglia. FIG. 3A schematically illustrates a transverse cross-sectional view of a spinal cord 402 surrounded by dura 404. The spinal cord 402 includes a plurality of levels from which spinal nerves 412a and 412b extend. In at least some spinal cord levels, the spinal nerves 412a and 412b extend bilaterally from the spinal cord 402. In FIG. 3A, the spinal nerves 412a and 412b attach to the spinal cord 402 via corresponding dorsal roots 414a and 414b and corresponding ventral (or anterior) roots 416a and 416b. Typically, the dorsal roots 414a and 414b relay sensory information into the spinal cord 402 and the ventral roots 416a and 416b relay motor information outward from the spinal cord 402. Dorsal root ganglia ("DRG") 420a and 420b are nodules of cell bodies that are disposed along the dorsal roots 416a and 416b in proximity to the spinal cord 402.

Figure 3B:
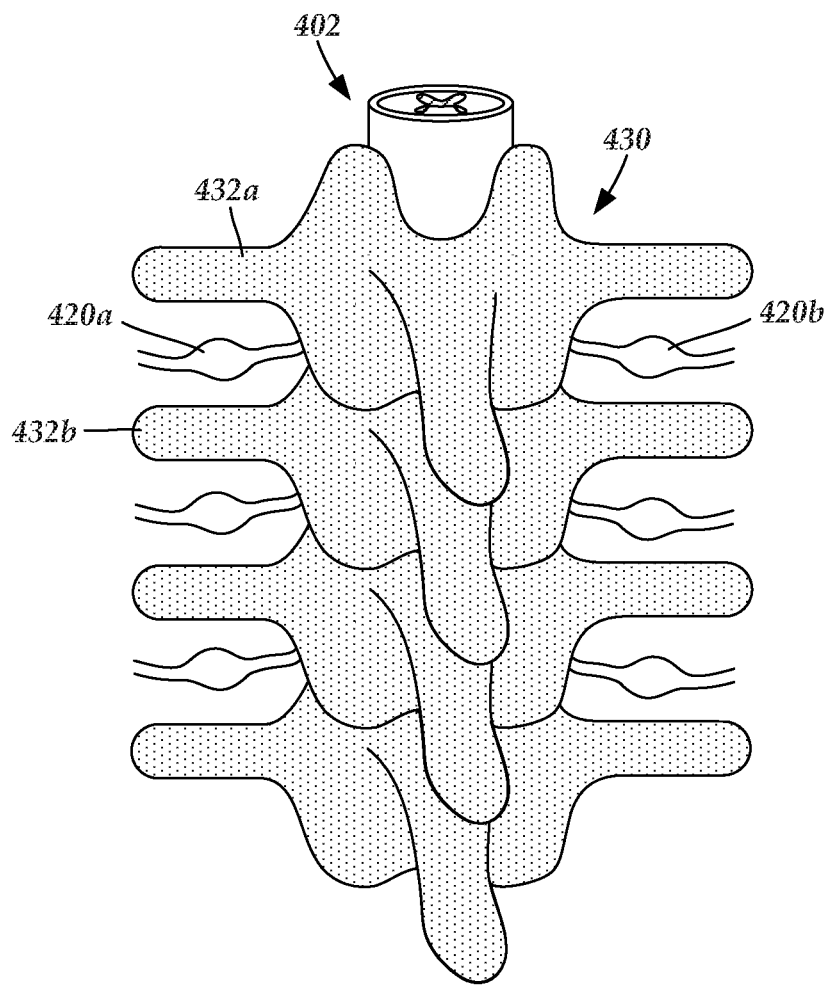
FIG. 3B is a schematic perspective view of a portion of the spinal cord of FIG. 3A disposed in a portion of a vertebral column with the dorsal root ganglia of FIG. 3A extending outward from the vertebral column.

FIG. 3B schematically illustrates a perspective view of a portion of the spinal cord 402 disposed along a portion of a vertebral column 430. The vertebral column 430 includes a plurality of stacked vertebrae, such as vertebrae 432a and 432b, and a plurality of DRGs 420a and 420b extending outwardly bilaterally from the spinal cord 402.

Figure 3C:
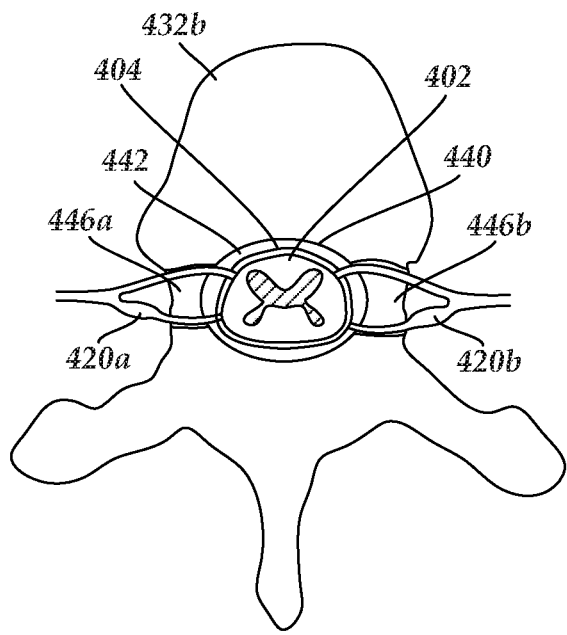
FIG. 3C is a schematic top view of a portion of the spinal cord of FIG. 3A disposed in a vertebral foramen defined in a vertebra of the vertebral column of FIG. 3B, the vertebra also defining intervertebral foramina extending between an outer surface of the vertebra and the vertebral foramen, the intervertebral foramina providing an opening through which the dorsal root ganglia of FIG. 3B can extend outward from the spinal cord of FIG. 3B.

FIG. 3C schematically illustrates a top view of a portion of the spinal cord 402 and dura 404 disposed in a vertebral foramen 440 defined in the vertebra 432b. The vertebrae 432 are stacked together and the vertebral foramina 440 of the vertebrae collectively form a spinal canal through which the spinal cord 402 extends. The space within the spinal canal between the dura 404 and the walls of the vertebral foramen 440 defines the epidural space 442. Intervertebral foramina 446a and 446b defined bilaterally along sides of the vertebra 432b form openings through the vertebra 432b between the epidural space 442 and the environment external to the vertebra 432b.

Figure 3D:
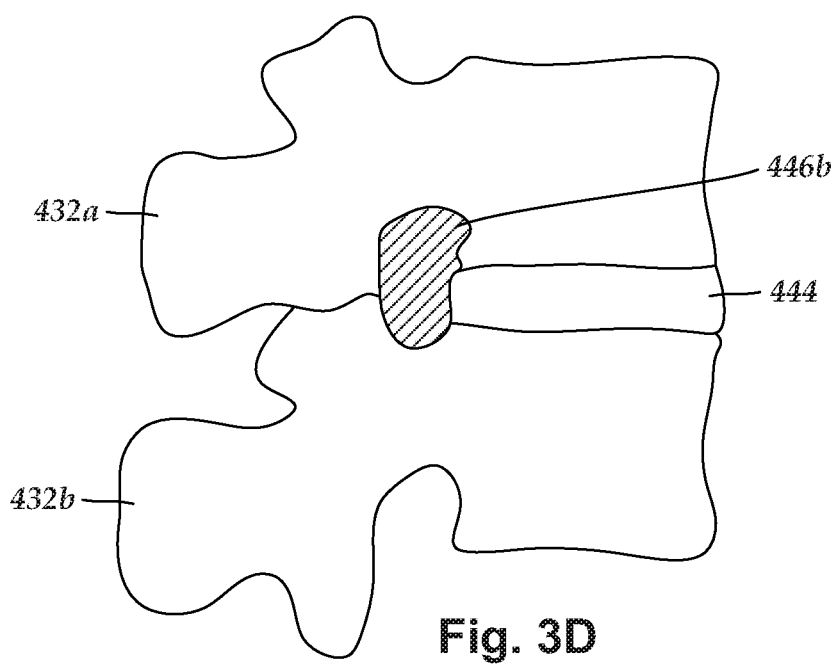
FIG. 3D is a schematic side view of two vertebrae of the vertebral column of FIG. 3B, the vertebrae defining an intervertebral foramen through which the dorsal root ganglia of FIG. 3B can extend outward from the spinal cord of FIG. 3B.

FIG. 3D schematically illustrates a side view of two vertebrae 432a and 432b coupled to one another by a disc 444. In FIG. 3D, the intervertebral foramen 446b is shown defined between the vertebrae 432a and 432b. The intervertebral foramen 446b provides an opening for one or more of the dorsal root 414b, ventral root 416b, and DRG 420b to extend outwardly from the spinal cord 402.

To facilitate stimulation of the dorsal root ganglion (DRG), the distal end of the lead body can have a hook or coil shape to fit around at least a portion of the DRG. In at least some embodiments, the lead is implanted retrograde and perpendicular, or substantially perpendicular, to the DRG 420a and the dorsal root 414a extending from the DRG. In at least some embodiments, the portion of the lead extending from the hook-shaped or coil-shaped distal end is arranged to form an angle of at least 45°, 50°, 60°, 70°, 80°, or 85° with the dorsal root 414a. In at least some embodiments, the hook-shaped or coil-shaped distal end of the lead body is isodiametric. In at least some embodiments, the hook-shaped or coil-shaped distal end of the lead body is also isodiametric with the remainder of the lead.

FIG. 4A illustrates one embodiment of a lead 106 with a distal end 118 of the lead having a hook-shaped distal end to fit around the DRG 420*a*. In at least some embodiments, the hook-shaped distal end extends around at least 40%, 50%, 60%, 70%, 75%, 80%, 90%, 95%, or 100% of the circumference of the DRG 420*a*.

FIG. 4B illustrates one embodiment of a lead 106 with a distal end 118 of the lead having a coil-shaped distal end to fit around a portion of the DRG 420*a*. The coil-shaped distal end may include any number of full turns (360° turn) around the DRG 420*a* including, for example, at least one, two, or three full turns. The coil-shaped distal end may also include a partial turn (less than 360° turn). The turns of the coil-shaped distal end may be situated immediately adjacent to each other in a touching arrangement, as illustrated in FIG. 4B, or the turns may be separated from each other or any combination thereof.

FIG. 5A illustrates one embodiment of a distal end 118 of a lead 106 formed into a hook shape. A series of electrodes 134 are provided along the distal end 118 of the lead 106. It will be recognized that the distal end 118 of lead 106 in this embodiment, as well as in those embodiments illustrated in FIGS. 5B-8B, also corresponds to the distal end of the lead body of lead 106. With respect to the designation of the distal end, the terms "lead" and "lead body" may be used interchangeably.

In this particular embodiment of FIG. 5A, each of the electrodes 134 is a ring electrode that extends around the circumference of the lead at that position along the distal end of the lead body of lead 106. Providing multiple electrodes allows the practitioner to select which electrodes are to be used to provide stimulation. The practitioner may use any combination of the electrodes and the selection of electrodes may change over time.

FIG. 5B illustrates another embodiment of a distal end 118 of a lead 106 formed into a hook shape. A series of electrodes 134 are provided along the distal end 118 of the lead 106. In this particular embodiment, each of the electrodes 134 is a segmented electrode that extends around only a portion of the circumference of the lead 106. For example, a segmented electrode may extend around no more than 75%, 50%, 40%, 30%, 25%, or less of the circumference of the lead. In the illustrated embodiment, the segmented electrodes 134 are disposed on the interior surface of the hooked distal end 118 so that when the lead 106 is implanted with the hook around the DRG (for example, as illustrated in FIG. 4A), the segmented electrodes 134 are adjacent to the DRG.

One possible advantage of using segmented electrodes over ring electrodes is that the stimulation current from a segmented electrode is more directed instead of being distributed around the circumference of the lead which is generally the case for a ring electrode. This may be beneficial to more directly target the DRG and, at least in some cases, to reduce the inadvertent stimulation of other tissue, including other nerve or spinal cord tissue, in the neighborhood of the DRG. Inadvertent stimulation of the other tissue may result in side-effects which may be deleterious.

FIG. 5B illustrates a single segmented electrode 134 at each position along the length of the distal end 118 of the lead 106. It will be recognized, however, that sets of segmented electrodes can be provided at each position along the length of the lead with the member electrodes of each set distributed around the circumference of the lead at that position. For example, each set of segmented electrodes can include two, three, four, five, six, or more segmented electrodes distributed around the circumference of the lead at the same longitudinal position along the lead. Suitable examples of leads with sets of segmented electrodes can be found in, for example, U.S. Patent Applications Publication Nos. 2010/0268298; 2011/0005069; 2011/0078900; 2011/0130817; 2011/0130818; 2011/0238129; 2011/0313500; 2012/0016378; 2012/0046710; 2012/0165911; 2012/0197375; 2012/0203316; 2012/0203320; and 2012/0203321; and U.S. Provisional Patent Application Ser. No. 61/651,822, all of which are incorporated herein by reference. An advantage of using these sets of segmented electrodes is that the practitioner can select which electrodes from a set to use for stimulation. Moreover, if the distal end of the lead is bent or coiled by the practitioner, the practitioner may have less concern regarding whether the segmented electrodes are positioned properly on the hook or coil (e.g., on the interior surface of the hook or coil) because at least one segmented electrode of each is set is likely to be properly positioned. Markers may be provided on or within the lead to identify the relative orientation of the sets of segmented electrodes or the terminal at the proximal end of the lead that corresponds to a particular segmented electrode or both. Examples of suitable markers can be found in, for example, U.S. patent application Ser. Nos. 13/176,595 and 13/369,013 and U.S. Provisional Patent Application Ser. Nos. 61/591,046; and 61/617,922, all of which are incorporated herein by reference.

Other types of electrodes can be used including, for example, a tip electrode at the distal tip of the lead. It will be recognized that a lead may include any combination of segmented electrodes, ring electrodes, and other types of electrodes in any arrangement along the distal end of the lead. It will also be recognized that the lead may include one or more additional electrodes (for example, segmented electrodes or ring electrodes or any combination thereof) on the portion of the lead that does not form the hook or coil (e.g., the portion of the lead adjacent the hook-shaped or coil-shaped distal end of the lead.) These considerations regarding the electrodes and their arrangement, as described with respect to the embodiments illustrated in FIGS. 5A and 5B, also apply to embodiments of a lead with a coiled distal end (see, for example, FIG. 4B), as well as the remainder of the lead embodiments described below including the embodiments illustrated in FIGS. 6A-8B.

There are a variety of arrangements for providing a hook or coil shape to the distal end of the lead. In some embodiments, the lead is manufactured with the distal end in the hook or coil shape. In some embodiments, the practitioner may be able to modify the hook or coil shape provided during manufacture by, for example, bending or unbending the lead prior to implantation. In other embodiments, the hook or coil shape may be unmodifiable.

In other embodiments, the lead may incorporate a bendable shaping member within the distal end of the lead. The bendable shaping member is arranged so that a practitioner can bend the distal end of the lead into the desired hook or coil shape prior to, or during, the lead implantation procedure and the bendable shaping member will retain that shape thereafter. The bendable shaping member can be, for example, a metal or flexible plastic wire that retains its shape when bent. Typically, the bendable shaping member is not electrically coupled to the electrodes or terminals and, in at least some embodiments, the bendable shaping member is substantially thicker (for example, 1.5, 2, 3, 4, 5, or more times thicker) than the conductors coupling the electrodes to the terminals. For example, the bendable shaping member can be made of titanium, stainless steel, tungsten, a shape memory material such as Nitinol™, or the like. Preferably, the bendable shaping member is made of a material that is reversibly bendable (i.e., the bendable shaping member can be bent back to the original shape). The bendable shaping member permits formation of a hook or coil shape in the distal end of the lead by bending of the distal end of the lead into the hook or coil shape and the bendable shaping member is configured and arranged to retain the distal end of the lead in the hook or coil shape without external force being applied FIGS. 6A and 6B illustrate one embodiment of a distal end 118 of a lead 106 that has electrodes 134 and incorporates a bendable shaping member 602 within the lead. FIG. 6A illustrates the lead 106 in an unbent condition and FIG. 6B illustrates the lead 106 in one embodiment of a hook shape. It will be understood that the lead can be bent into other hook or coil shapes. The bendable shaping member 602 may be disposed anywhere within the lead including, but not limited to, embedded in a lead, disposed within one or more lumens of the lead, or disposed on a surface of the lead. The lead may include more than one bendable shaping member 602. The bendable shaping member 602 may be disposed only at the distal end of the lead or may extend further along the lead; even to the proximal end of the lead in some embodiments.

In yet other embodiments, a removable guidewire or removable stylet may be used to bend the lead prior to, or during, the implantation procedure. The guidewire or stylet may be inserted into a lumen extending along at least a portion, including the distal end, of the lead prior to, or during, the implantation procedure for the lead.

FIGS. 7A and 7B illustrate one embodiment of a distal end 118 of a lead 106 that has electrodes 134. FIG. 7A illustrates the lead 106 in an unbent condition and without the guidewire or stylet inserted into the lead and FIG. 7B illustrates the lead 106 with the guidewire or stylet 704 inserted and causing the distal end of the lead to have a bent shape. It will be understood that the lead can be bent into other hook or coil shapes using a guidewire or stylet. In at least some embodiments, the guidewire or stylet is inserted into a lumen extending along at least a portion of the lead including, preferably, the distal end 118 of the lead. It will also be understood that more than one guidewire or stylet can be used and may be inserted into the same lumen or different lumens within the lead.

FIGS. 8A and 8B illustrate an embodiment of a lead 106 and a guidewire or stylet 704 that incorporates an outer sheath 706 and an inner member 708. Preferably, the outer sheath 706 and inner member 708 are slidably engaged to allow the outer sheath 706 to be retracted to expose a portion of the inner member 708, or to allow the inner member to advance out of the outer sheath to expose the inner member, or to allow both retraction of the outer sheath and advancement of the inner member. In operation the outer sheath 706 of the guidewire or stylet 704 is arranged to maintain the guidewire or stylet 704 in a linear configuration, as illustrated in FIG. 8A. This facilitates insertion of the lead 106 into the patient. The outer sheath 706 may then be partially, or fully, retracted, as illustrated in FIG. 8B, (or advancement of the inner member out of the outer sheath) to expose at least a portion of the inner member 708. The inner member 708 is arranged to bend to form the desired hook or coil shape. Examples of a guidewire or stylet with such an arrangement are described in U.S. Patent Application Publication No. 2009/0187222, which is incorporated herein by reference.

In some embodiments, a guidewire or stylet may remain in the lead after implantation to retain the bent or coiled shape of the distal end of the lead. In other embodiments, the guidewire or stylet may be removed after implantation and the distal end of the lead is arranged to maintain the bent or coil shape on its own or the practitioner fastens the lead to surrounding tissue (for example, using one or more sutures, staples, adhesives, lead anchors, or other fastening devices or any combination thereof) to retain the bent or coil shape or the surrounding tissue maintains the bent or coil shape of the distal end of the lead by preventing or reducing the likelihood of unbending or uncoiling or any combination of these mechanisms.

The leads described herein can be implanted using any suitable implantation method. A novel method for implanting the leads described herein is presented in U.S. Provisional Patent Application Ser. No. 61/651,815, incorporated herein by reference.

Figure 9:
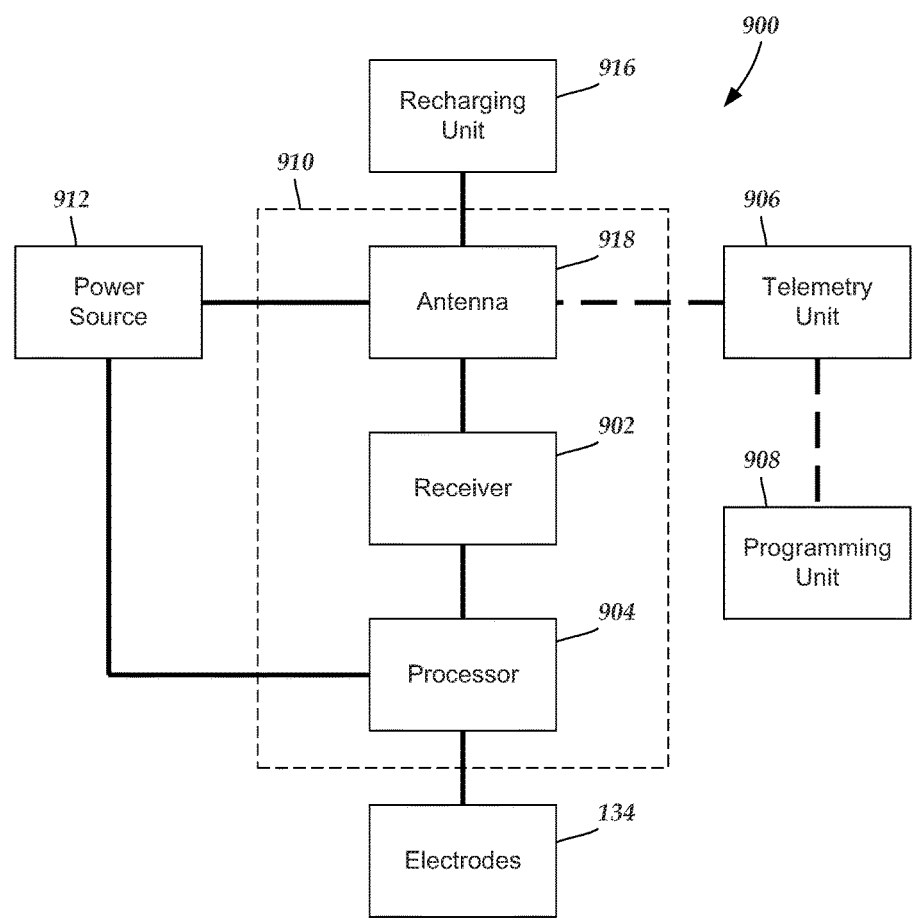
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead, comprising:
   a lead body having a distal portion, a proximal portion, and a longitudinal length;
   a plurality of electrodes disposed along the distal portion of the lead body;
   a plurality of terminals disposed on the proximal portion of the lead body;
   a plurality of conductors electrically coupling the electrodes to the terminals; and
   a bendable shaping member that is reversibly bendable and is permanently disposed solely within the distal portion of the lead body, wherein the bendable shaping member is not electrically coupled to any of the electrodes or the terminals, wherein the bendable shaping member is configured to permit formation of a hook or coil shape in the distal portion of the lead body by bending of the distal portion of the lead body into the hook or coil shape, wherein the bendable shaping member is configured to retain the distal portion of the lead body in the hook or coil shape without external force being applied.

2. The implantable electrical stimulation lead of claim 1, wherein the bendable shaping member is embedded in the lead body.

3. The implantable electrical stimulation lead of claim 1, wherein the bendable shaping member is disposed on a surface of the lead body.

4. The implantable electrical stimulation lead of claim 1, wherein the bendable shaping member comprises a metal or plastic wire.

5. The implantable electrical stimulation lead of claim 1, wherein the plurality of electrodes comprises a plurality of segmented electrodes, wherein each of the segmented electrodes extends around no more than 75% of a circumference of the lead body.

6. The implantable electrical stimulation lead of claim 1, wherein the bendable shaping member comprises a shape memory material.

7. The implantable electrical stimulation lead of claim 1, wherein the bendable shaping member has a thickness that is at least 1.5 times a thickness of any one of the conductors.

8. The electrical stimulation lead of claim 5, wherein the plurality of electrodes further comprises at least one ring electrode.

9. The electrical stimulation lead of claim 5, wherein the plurality of electrodes are all segmented electrodes, wherein each of the segmented electrodes extends around no more than 40% of a circumference of the lead body.

10. The electrical stimulation lead of claim 1, wherein the lead body is isodiametric.

11. The electrical stimulation lead of claim 1, wherein the electrical stimulation lead comprises a plurality of bendable shaping members.

12. The electrical stimulation lead of claim 1, wherein the bendable shaping member is disposed in a lumen of the lead.

13. The electrical stimulation lead of claim 1, wherein the bendable shaping member is reversibly bendable and retains a bent shape when bent to the bent shape.

14. A method of implanting an electrical stimulation lead, the method comprising:
   providing an electrical stimulation lead comprising a lead body having a distal portion, a proximal portion, and a longitudinal length, a plurality of electrodes disposed along the distal portion of the lead body; a plurality of terminals disposed along the proximal portion of the lead body, a plurality of conductors electrically coupling the electrodes to the terminals, and a bendable shaping member that is reversibly bendable and is permanently disposed solely within the distal portion of the lead body, wherein the bendable shaping member is not electrically coupled to any of the electrodes or the terminals, wherein the bendable shaping member is configured to permit formation of a hook or coil shape in the distal portion of the lead body by bending of the distal portion of the lead body into the hook or coil shape;

shaping the distal portion of the lead body of the electrical stimulation lead into the hook or coil shape by bending the bendable shaping member, wherein the bendable shaping member is configured to retain the distal portion of the lead body in the hook or coil shape without external force being applied; and implanting the electrical stimulation lead with the distal portion of the lead body in the hook or coil shape disposed around a dorsal root ganglion of a patient.

15. The method of claim 14, wherein the plurality of electrodes comprises a plurality of segmented electrodes, wherein each of the segmented electrodes extends around no more than 40% of a circumference of the lead body.

16. The method of claim 14, wherein the bendable shaping member is embedded in the lead body.

17. The method of claim 14, wherein the bendable shaping member is disposed on a surface of the lead body.

18. The method of claim 14, wherein the bendable shaping member comprises a metal or plastic wire.

19. The method of claim 15, wherein the plurality of electrodes further comprises at least one ring electrode.

20. The method of claim 14, wherein the electrical stimulation lead comprises a plurality of bendable shaping members.

* * * * *